US012758187B2

(12) United States Patent
Arndt

(10) Patent No.: US 12,758,187 B2
(45) Date of Patent: Oct. 13, 2026

(54) ULTRASONIC SYSTEM FOR POINT OF CARE AND RELATED METHODS

(71) Applicant: KBR Wyle Services, LLC, Houston, TX (US)

(72) Inventor: F Jeffrey Scott Arndt, Fairfax, VA (US)

(73) Assignee: KBR Wyle Services, LLC, Houston, TX (US)

( * ) Notice: Subject to any disclaimer, the term of this patent is extended or adjusted under 35 U.S.C. 154(b) by 66 days.

(21) Appl. No.: 18/191,741

(22) Filed: Mar. 28, 2023

(65) Prior Publication Data

US 2023/0309963 A1 Oct. 5, 2023

Related U.S. Application Data

(60) Provisional application No. 63/325,891, filed on Mar. 31, 2022.

(51) Int. Cl.
*A61B 8/00* (2006.01)
*A61B 8/08* (2006.01)

(52) U.S. Cl.
CPC .......... *A61B 8/4455* (2013.01); *A61B 8/4227* (2013.01); *A61B 8/4488* (2013.01); *A61B 8/5276* (2013.01)

(58) Field of Classification Search
CPC ... A61B 8/4455; A61B 8/4227; A61B 8/4488; A61B 8/5276; A61B 8/0833; A61B 8/4427; A61B 8/4494; A61B 8/54; A61B 8/4236; A61B 8/429; G01S 7/5205; G01S 15/8915; G01S 15/8936
See application file for complete search history.

(56) References Cited

U.S. PATENT DOCUMENTS

| | | | | |
|---|---|---|---|---|
| 2003/0127949 | A1* | 7/2003 | Nagahara | B06B 1/0622 310/334 |
| 2007/0078345 | A1 | 4/2007 | Mo et al. | |

(Continued)

FOREIGN PATENT DOCUMENTS

| | | | |
|---|---|---|---|
| EP | 3881770 | A1 | 9/2021 |
| WO | 2020215075 | A1 | 10/2020 |

OTHER PUBLICATIONS

Eastridge BJ, Hardin M, Cantrell J, et al. Died of wounds on the battlefield: causation and implications for improving combat casualty care. Journal of Trauma and Acute Care Surgery. 2011;71(1):S4-S8.

(Continued)

*Primary Examiner* — Alexei Bykhovski
(74) *Attorney, Agent, or Firm* — Gary M. Machetta

(57) ABSTRACT

An ultrasonic diagnostic system that may include a transducer having a deformable housing, at least one securing member, and an ultrasonic transducer array disposed in the deformable housing. The transducer array may include a plurality of transducer elements and the deformable housing flexes to conform to a surface contour of a selected region on a body of a patient. An information processing device may be in signal communication with the transducer and may include at least one beamforming algorithm and at least one image enhancement algorithm. The at least one beamforming algorithm may be configured to correct for arbitrary positions of the transducer elements of the ultrasonic transducer array.

16 Claims, 4 Drawing Sheets

(56) References Cited

U.S. PATENT DOCUMENTS

| | | | | |
|---|---|---|---|---|
| 2018/0113205 | A1 | 4/2018 | Sikdar et al. | |
| 2018/0130457 | A1 | 5/2018 | Hakkens et al. | |
| 2018/0214130 | A1* | 8/2018 | Hossack | A61B 8/4209 |
| 2019/0046158 | A1* | 2/2019 | Kroon | A61B 8/4236 |
| 2019/0125296 | A1* | 5/2019 | Keidar | A61B 8/4472 |
| 2020/0121281 | A1* | 4/2020 | Dagdeviren | A61B 8/4209 |
| 2021/0068792 | A1* | 3/2021 | Sornes | G01S 7/52026 |
| 2023/0309963 | A1 | 10/2023 | Arndt | |
| 2024/0159897 | A1* | 5/2024 | D'Hooge | G01S 7/52036 |

OTHER PUBLICATIONS

King DR. Thirty consecutive uses of a hemostatic bandage at a US Army combat support hospital and forward surgical team in Operation Iraqi Freedom. Journal of Trauma and Acute Care Surgery. 2011;71(6):1775-1778.

Eastridge BJ, Mabry RL, Seguin P, et al. Death on the battlefield (2001-2011): implications for the future of combat casualty care. Journal of trauma and acute care surgery. 2012;73(6):S431-S437.

Alarhayem A, Myers JG, Dent D, et al. Time is the enemy: mortality in trauma patients with hemorrhage from torso injury occurs long before the "golden hour". The American Journal of Surgery. 2016;212(6):1101-1105.

Bogert JN, Patel BM, Johnson DJ. Ultrasound optimization for resuscitative endovascular balloon occlusion of the aorta. Journal of Trauma and Acute Care Surgery. 2017;82(1).

Keenan S, Riesberg JC. Prolonged Field Care: Beyond the "Golden Hour". Wilderness & Environmental Medicine. 2017;28(2, Supplement):S135-S139.

Sikdar S, Wei Q, Cortes N. Dynamic ultrasound imaging applications to quantify musculoskeletal function. Exercise and sport sciences reviews. Jul. 2014;42(3):126.

Sikdar S, Shah JP, Gebreab T, et al. Novel applications of ultrasound technology to visualize and characterize myofascial trigger points and surrounding soft tissue. Archives of physical medicine and rehabilitation. 2009;90(11):1829-1838.

Bird M, Le D, Shah J, et al. Characterization of local muscle fiber anisotropy using shear wave elastography in patients with chronic myofascial pain. Paper presented at: 2017 IEEE International Ultrasonics Symposium (IUS)2017.

Rostaminia G, Wei Q, Tomezsko J. Posterior perineal translevator hernia: application of MRI, 3D ultrasound, and computerized modeling. International urogynecology journal. 2018;29(10):1559-1561.

Akhlaghi N, Dhawan A, Khan A, et al. Sparsity Analysis of a Sonomyographic Muscle-Computer Interface. IEEE Transactions on Biomedical Engineering. 2019.

Wei Qi, Sikdar Diddhartha, Chitnis Parag, Patient-Specific Studies of Pelvic Floor Biomechanics Using Imaging, Springer International Pubishing AG 2017.

Patwardhan S, Dhawan AS, Mukherjee B, Alzamani M, Joiner WM, Sikdar S. Evaluation of the Role of Proprioception During Proportional Position Control Using Sonomyography: Applications in Prosthetic Control. Paper presented at: 2019 IEEE 16th International Conference on Rehabilitation Robotics (ICORR)2019.

Michailovich OV, Tannenbaum A. Despeckling of medical ultrasound images. IEEE Trans Ultrason Ferroelectr Freq Control. 2006;53(1):64-78.

Acoustic Output Measurement Standard for Diagnostic Ultrasound Equipment, Revision 3. In: National Electrical Manufacturers Association; 2009.

Jensen JA, Nikolov SI, Gammelmark KL, Pedersen MH. Synthetic aperture ultrasound imaging. Ultrasonics. 2006;44:e5-e15.

Stankwitz H, Kosek M. Sparse aperture fill for SAR using super-SVA. Paper presented at: Proceedings of the 1996 IEEE National Radar Conference1996.

AlMohimeed I, Agarwal M, Ono Y. Wearable Ultrasonic Sensor Using Double-Layer PVDF Films for Monitoring Tissue Motion. Paper presented at: 2018 IEEE Canadian Conference on Electrical & Computer Engineering (CCECE)2018.

Zangabad RP, Springeling G, Noothout E, et al. A Kerfless PVDF Array for Photoacoustic Imaging. Paper presented at: 2018 IEEE International Ultrasonics Symposium (IUS)2018.

Zou KH, Warfield SK, Bharatha A, et al. Statistical validation of image segmentation quality based on a spatial overlap index1: scientific reports. Acad Radiol. 2004;11(2):178-189.

Malik Jitendra, Belongie Serge, Leung Thomas and Shi Jianbo, Contour and Texure Analysis for Image Segmentation, International Journal of Computer Vision 43(1), 7-27, 2001.

Patent Cooperation Treaty, International Searching Authority, International Search Report and Written Opinion dated Dec. 14, 2023 for International Application No. PCT/US2023/065064 filed Mar. 28, 2023, 15 pages.

European Patent Office, Supplemental Partial European Search Report dated Feb. 4, 2026 for European Application No. EP23782020.4 filed Oct. 28, 2024, 11 pages.

* cited by examiner

ULTRASONIC SYSTEM FOR POINT OF CARE AND RELATED METHODS

CROSS REFERENCE TO RELATED APPLICATIONS

This application claims the benefit of U.S. Provisional Application No. 63/325,891, filed Mar. 31, 2022, which is incorporated herein by reference in its entirety.

BACKGROUND

Technical Field

Embodiments described herein generally relate to devices and related method that may be used by medical personnel to perform casualty care and other resuscitative procedures.

Background

In some situations, early pre-hospital intervention in a patient suffering a trauma may be critical in extending a "golden hour" for that patient and ultimately improve chances for survival. However, conventional techniques for rendering such medical care in austere locations far from a medical facility can have considerable shortcomings. For example, medical intervention employed during point-of-care and enroute care may require care givers to have extensive and specializing training to operate diagnostic equipment. Further, personnel may find it difficult, or impossible, to use such diagnostic equipment while also administering treatment for the patient.

SUMMARY

In examples, disclosed is an ultrasonic diagnostic system, including a transducer including a deformable housing configured to conform to a surface contour of a selected region, and an ultrasonic transducer array disposed in the deformable housing and comprising a plurality of transducer elements configured to assume arbitrary positions when the housing is deformed. In examples, the transducer may be configured to collect image data while in a fixed position and to communicate the image data to an information processing device that may include at least a beamforming algorithm or an image enhancement algorithm.

In examples, each transducer element of the ultrasonic transducer array may be moveable relative to one another.

In examples, each transducer element of the ultrasonic transducer array may include a conductive element between 6 and 100 μm in length and between 20 and 100 μm in width.

In examples, a pitch of the ultrasonic transducer array may be in the range of about 450 μm to 710 μm, and wherein a center frequency for the transducer array is about 1.2 MHz to about 5.7 MHz.

In examples, the at least one beamforming algorithm may be configured to correct for: (i) changes in relative locations of the transducer elements of the transducer array, and (ii) changes in relative orientations of the transducer elements.

In examples, the least one information processing device further may include a distance correction algorithm configured to correct for changes in distance between the transducer elements and internal body tissue.

In examples, the least one information processing device may include a motion correction algorithm configured to correct for the displacement of an internal feature below the surface contour and one or more of the plurality of transducer elements. In examples, the least one information processing device further may include a motion correction algorithm configured to correct for the displacement of a feature of interest inside a body of a patient, wherein the feature of interest comprises: (i) bodily tissue, or (ii) a fluid.

In examples, the at least one image enhancement algorithm may be configured to perform segmentation of an image.

In examples, the transducer may include a securing member.

In examples, the diagnostic system may include a display device in signal communication with the information processing device.

In examples, disclosed is a method for collecting image data including, securing a transducer to a selected location, the transducer having a deformable housing, at least one securing member, and an ultrasonic transducer array disposed within the deformable housing; collecting image data by operating the transducer via an information processing device while keeping the transducer stationary relative to the selected location; correcting the collected data using at least one beamforming algorithm, wherein the at least one beamforming algorithm corrects for arbitrary positions of one or more transducer elements of the ultrasonic transducer array; and enhancing an image representative of the collected data using and at least one image enhancement algorithm.

In examples, the method may include displaying the enhanced image on a display device.

In examples, securing the transducer may include one of: (i) securing the transducer using an adhesive, and (ii) compressing the transducer to the selected location using a band.

In examples, the method may include correcting the image data collected to reduce errors arising from relative motion between the transducer and a region of interest below a surface of the selected location.

In examples, the selected location may include a body region of a patient and the transducer is secured to a cutaneous surface of the body of the patient.

In examples, the method may include correcting the image data collected to reduce errors arising from relative motion between the transducer and an internal organ within the body of the patient.

In examples, disclosed is a processor-readable medium having a machine program embedded therein and accessible to at least one processor for executing the machine program, the at least one processor being associated with a transducer configured to acquire data below a selected surface, wherein the transducer may include an ultrasonic transducer array having a plurality of transducer elements, wherein the machine program may include instructions to operate the transducer to collect data; instructions to correct the collected data for arbitrary positions of transducer elements of the ultrasonic transducer array; and instructions to enhance an image representative of the collected data.

In examples, the transducer is configured to acquire data representative of internal body tissue.

In examples, the present disclosure provides an ultrasonic diagnostic system. In examples, the present disclosure provides a method for performing diagnostics. In examples, the diagnostic system as described may include a transducer having a deformable housing and at least one securing member. In examples, the system may include an ultrasonic transducer array disposed in a deformable housing. The transducer array may include a plurality of transducer elements. In examples, the deformable housing may be configured to conform to a surface contour of a selected region on a body of a patient. In examples, the deformable housing may be flexible, elastic, stretchable, compressible or any combination thereof. In examples, the diagnostic system may include or be in communication with an information processing device. In examples, the information processing device may be in signal communication with the transducer. In examples, the least one information processing device may include at least one beamforming algorithm and at least one image enhancement algorithm. In examples, a beamforming algorithm may be configured to correct for arbitrary positioning of the transducer elements of the ultrasonic transducer array.

In examples, disclosed is a method for performing a diagnostic on a patient. The method may include the steps of securing a diagnostic system at a selected location. In examples, the selected location may be on a location on the body of a patient. In examples, the diagnostic system may include a transducer having a deformable housing and at least one securing member. In examples, the diagnostic system may include a transducer array disposed on or in the deformable housing. In examples, the method may include collecting data by using at least one information processing device to operate the transducer of the diagnostic system. In examples, the transducer may be stationary relative to the selected location while data is collected. In examples, the method may include correcting the collected data using a beamforming algorithm. In examples, a beamforming algorithm may be configured to correct for arbitrary positions of one or more transducer elements of the ultrasonic transducer array. In examples, the method may include enhancing an image representative of the collected data using and an image enhancement algorithm.

In examples, a processor-readable medium having a machine program embedded therein and accessible to at least one processor for executing the machine program may be associated with a transducer configured to acquire ultrasonic diagnostic data. In examples, the ultrasonic diagnostic data may be representative of internal body tissue. In examples, the transducer may include an ultrasonic transducer array having a plurality of transducer elements. In examples, the machine program may include instructions to operate the transducer to collect data. In examples, the instructions may be configured to correct the collected data for arbitrary positioning of transducer elements of the ultrasonic transducer array. In examples, instructions may be configured to enhance an image representative of the collected data.

In examples, the system and methods as described herein may provide a partial or complete "hands-free" operation of diagnostic equipment. This may enable medical personnel to perform other necessary resuscitative procedures while also operating the diagnostic equipment.

In examples, the system and methods as described herein may provide a diagnostic equipment that does not require extensive training to utilize. In examples, the system as described may be configured for used by non-medical personnel.

In examples, the system and methods as described may provide accurate information for guiding diagnoses and triaging. More generally, the system as described may provide a diagnostic equipment that may operate over communication systems that have relatively low bandwidth and/or are noisy.

It should be understood that examples of certain features of the disclosure have been summarized rather broadly in order that the detailed description thereof that follows may be better understood, and in order that the contributions to the art may be appreciated. There are, of course, additional features of the disclosure that will be described hereinafter and which will in some cases form the subject of the claims appended thereto.

BRIEF DESCRIPTION OF THE DRAWINGS

For detailed understanding of the present disclosure, references should be made to the following detailed description of the preferred embodiment, taken in conjunction with the accompanying drawings, in which like elements have been given like numerals and wherein.

DETAILED DESCRIPTION

Figure 1:
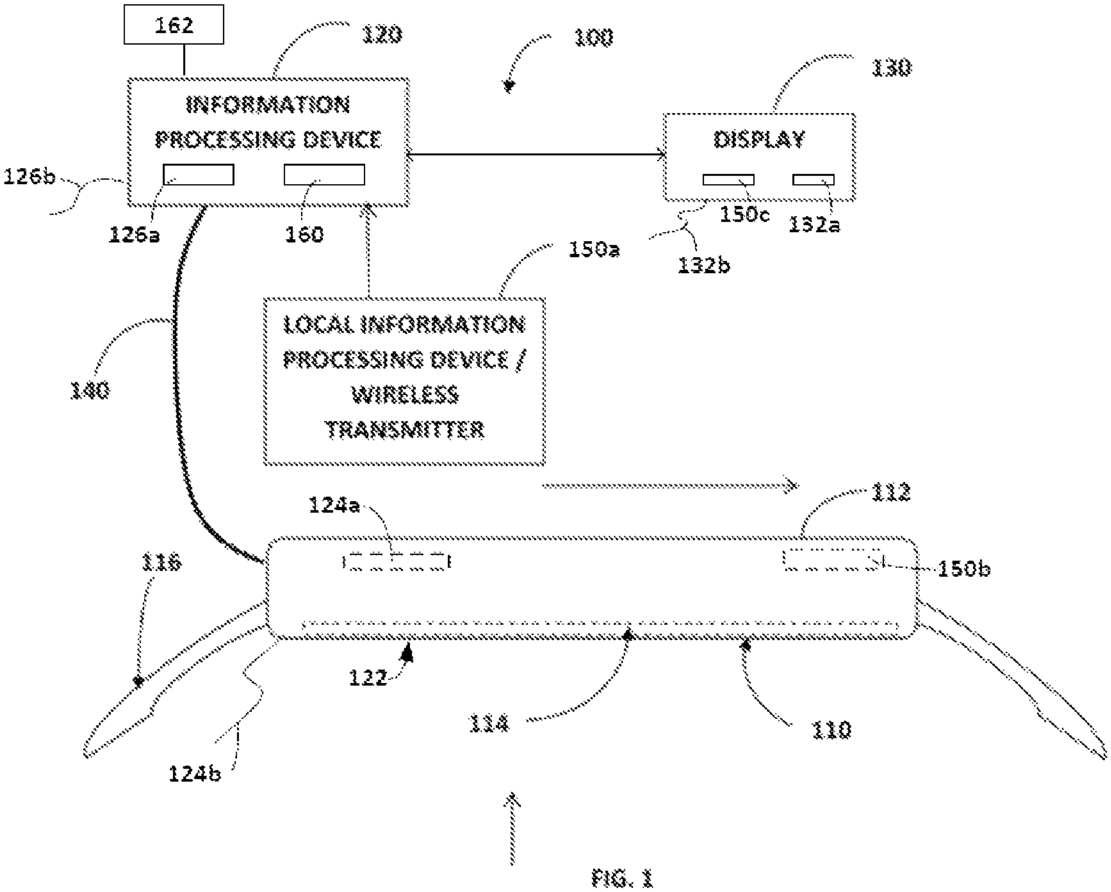
FIG. 1 schematically illustrates an embodiment of a diagnostic system according to the present disclosure.

In examples, the present disclosure provides a system and method for running a diagnostic. In examples, a diagnostic system may include an ultrasonic (US) diagnostic instrument to generate images. In examples, the ultrasonic diagnostic instrument may be or include a wearable device. In examples, the diagnostic system may be used to generate images of human internals. In examples, the diagnostic system may be used for assessing a traumatic injury. For ease of reference, the discussion below describes the system and method herein in reference to locating and characterizing injuries in a human truncal region. However, the diagnostic system and method as described may be used to examine any human body part including human extremities. It should also be understood that the system and method disclosed here in is not limited to application to human patients. In examples, the device may be used on plants and animals. In examples, the device may be used on inanimate objects.

In examples, the diagnostic system may be configured to provide real-time image-guidance.

In examples, a diagnostic system may include a transducer. In examples, the transducer may be hands-free, conformal ultrasound-imaging transducer. In examples, the transducer may be configured to be applied like a bandage. In examples, the transducer may be configured to be applied directly onto a bare surface, for example onto the bare portion of a body part of a patient. In examples, the transducer may be configured to be applied directly onto the skin of a patient.

In examples, the transducer may include an array of two or more transducer elements. In examples, the transducer may include a deformable housing. In examples, the array of transducer elements may be mounted onto and/or within the deformable housing. In examples, a transducer element may be a conductive element 6-100 μm long and 20-100 μm wide. In examples, the array of transducer elements may include transducer elements arranged at a pitch of about 450 μm to 710 μm. In examples, maintaining the pitch within this range may help avoid or diminish grating lobes for ultrasound transducer with about 1.2 MHz to about 5.7 MHz center frequency. In examples, low frequency operation may enable or improve imaging several centimeters deep. In examples, the transducer may include one or more securing members configured to secure the transducer to surface. In examples, the one or more securing members may detachably secure the transducer to a surface. In examples, the one or more securing members may be configured as extensions of and/or attachment to the deformable housing.

In examples, the diagnostic system may include an information processing device. In examples, the information processing device may include a processor and/or microcircuitry, or other computing device. In examples, the information processing device may include a memory. In examples, the information processing device may include instructions in the form of software, hardware, or a combination thereof. In examples, the information processing device may be configured to function as an imaging control and operating unit for the transducer. In examples, the information processing device may be an integral part of the diagnostic system together with the transducer. In examples, the information processing device may be physically separate from the transducer. In examples, the information processing device may be in communication with the transducer. In examples, the information processing device may be tethered to the transducer via a cable or like device. In examples, the information processing device may be configured to communicate with the transducer via a tethered connection, wirelessly, or a combination of both.

In examples, the diagnostic system may be portable. For purposes of this description a portable system is one that is sized relative to a human body of an average adult male. For purposes of this disclosure, portable is used to refer that an item may be carried by hand by a person. In examples, the diagnostic system may include one or more components each being independently portable. In examples, the diagnostic system may be completely portable having all components may be portable either together or independently. In examples, the diagnostic system may partially portable have some but not all components being portable. For example, the transducer and the information processing device may be parts of a single, integral, portable device. In examples, the transducer and the information processing device may be separate and/or separable independently portable devices. In examples, the transducer may be a portable device and the information processing device may not be a portable device. In examples, the one or more components of the diagnostic system may be portable but require being connected to a non-portable power source when in use. In examples, the transducer may not be a portable device and the information processing device may be portable. In examples, the diagnostic system is not portable with none of its components being portable either alone or in combination.

In examples, the diagnostic system may use a synthetic aperture beamforming (SAB) algorithm with optimization techniques to produce images (for example, images with brightness mode such as A-Mode, B-Mode, C-Mode, and M-Mode) from low-channel count US systems and an existing machine learning framework for image formation. The drive and control electronics can be miniaturized and powered by a battery or other suitable power source.

In examples, image-enhancement can utilize a local variation technique using modifications of Kruskal's algorithm, that is routinely used for segmenting land features (water, terrain, and human-made objects) from synthetic aperture radar (SAR) images and other types of imagery.

Referring to FIG. 1, there is schematically illustrated an example of a diagnostic system 100 according to the present disclosure. In examples, diagnostic system 100 may be deployed by personnel at point-of-care and/or enroute care. In examples, diagnostic system 100 may be used by non-medical personnel and/or for non-medical use.

In examples, the diagnostic system 100 may include a transducer 110 and an information processing device 120. In examples, the diagnostic system 100 may include one or more displays 130.

In examples, information encoded signals may be exchanged between these components by using physical carriers 140 and/or wireless transmission devices 150. In examples, a wireless transmission device 150 may include any suitable device for wireless communication that may be via local area network, a cellular network, a node network, wi-fi, Bluetooth, radio frequency, or any combination thereof. In examples, a wireless transmission device 150 may include one or more of a receiver, transmitter, transceiver or similar communication device. In examples, transducer 110 and/or the information processing device 120, and/or a display 130 may include and/or have access to or be coupled to a wireless transmission device 150 to enable communication with one or more other components of diagnostic system 100. In examples, the transducer 110 and the information processing device 120 may each include a wireless transmission device 150 (for example 150*a* and 150*b*). In examples, each component may have the same or different type of wireless transmission device 150. For example, the transducer 110 may include a transmitter and the information processing device 120 may include a receiver or transceiver. In examples, a display 130 may include a wireless transmission device 150*c* that is the same or different from the wireless transmission device of the information processing device 120 and/or of transducer 110.

In examples, electrical power may be provided by suitable power sources such as batteries, capacitors, and/or external power source. In examples, the diagnostic system may include a power source such as a battery or capacitor. In examples, the diagnostic system may be battery powered. In examples, the diagnostic system may be configured to connect to an external power supply. In examples, the diagnostic system may include a power source and be configured to connect to an external power supply. In examples, each component of a diagnostic system may be independently powered. For example, a transducer 110 may independently include a battery or capacitor 124*a* and/or be configured to connect to an external power supply 124*b*. Similarly, the information processing device 120 may independently include a battery or capacitor 126*a* and/or be configured to connect to an external power source 126*b*. In examples, the transducer may be configured to power the information processing device. In examples, the information processing device may be configured to power the transducer. In examples, the transducer and the information processing device may be configured to be powered by a common power source.

In examples, the transducer 110 may be a wearable transducer. In examples, transducer 110 may include a housing 112, one or more securing members 116, and a transducer array 114 of transducer elements 118. In examples, the transducer array 114 may be an ultrasonic transducer array. In examples, one or more transducer elements 118 may be ultrasonic transducer elements.

In examples, housing 112 may be formed of a deformable material. In examples, housing 112 may be formed of a material that allows the housing 112 to deform to seat contiguously along a surface. In examples, housing 112 can be deformed to seal contiguously along a surface of a section of a portion of the body of a patient. In examples, housing 112 can be deformed to seal contiguously along at least a surface of a section of a truncal region of a patient, such as the chest or abdomen. In examples, housing 112 may include a designated contact surface 122 that is configured to face the object onto which transducer 110 is affixed during use. In examples, contact surface 122 may physically contact the surface upon which transducer 110 is affixed during use. Example materials for the housing 112 include, but are not limited to, fabrics, plastics, elastomers, any combination thereof and/or other materials that have sufficient flexibility to physically adapt to a surface contour. In examples, housing 112 may include a bending mode based flexible piezoelectric micro ultrasonic transducer (PMUT) array or other fabricated flexible piezoelectric polymers.

In examples, the transducer of the diagnostic system may have any desirable and/or suitable shape. In examples, the shape as described herein may be the shape of the deformable housing at least prior to any deformation. In examples, the transducer of the diagnostic system may have a quadrilateral shape, a rounded shape, an irregular shape, a symmetrical or unsymmetrical shape. In examples, the transducer may have surface dimensions ranging from 0.2 in to 10 in. Depending on the shape, a surface dimension may independently be a surface length, surface width, surface diameter, surface axis, or longest or shortest surface distance between opposite sides. In examples, any one surface dimension may independently be 0.2 in, 0.3 in, 0.4 in, 0.5 in, 1 in, 2 in, 3 in, 4 in, 5 in, 6 in, 7 in, 8 in, 9 in, 10 in, or fall within any range defined by these examples.

The one or more securing members 116 may include any suitable structure that can assist with securing the transducer 110 to the surface upon which it is to be used. In examples, a securing member 116 may include one or more straps, belts, elastic bands, adhesive elements or any combination thereof. In examples, securing members 116 may be configured to removably affix the housing 112 securely to the surface on which the transducer 110 is to be used. In examples, the surface may be a surface of a portion of the body of a patient.

In examples, securing members 116 may be configured to keep the transducer 110 stationary relative to a cutaneous surface of the body while data is collected. For example, the securing members 116 may be configured to affix transducer 110 to a bare surface of the body of a patient.

In examples, the transducer 110 may be configured to obtain imaging data without requiring physical manipulation and/or movement. In examples, the transducer 110 may be able to obtain imaging data relying on the signals from the different transducer elements 118 that make up the transducer array 114. In examples, like the housing 112, the transducer array 114 may be deformable. In examples, transducer array 114 can be configured to bend, stretch, and twist as needed to conform to a surface upon which the transducer 110 is to be used, for example the surface of a at least a portion of the body of a patient. In examples, the transducer array 114 may utilize a construction known for medical applications such as elements having piezoelectric properties.

In examples, the transducer array 114 may be operated in conjunction with a beamforming algorithm as described in more detail later to obtain imaging data. Accordingly, in examples, once the transducer 110 and/or housing 112 of transducer 110 is secured to a surface, such as for example the surface of a portion of a body of a patient, it can obtain imaging data while the securing members 116 keep the transducer 110 and/or housing 112 at a fixed location. In this manner, a user may perform other activities while obtain imaging data via transducer 110. This may be an advantage, for example, when medical personnel is attending to a trauma patient, as the medical personnel may be freed to perform other activities while transducer 110 obtains imaging data that can further assist the personnel in attending to the patient.

In examples, the beamforming algorithm may be stored and executed on the information processing device 120. In examples, the information processing device 120 may be or include a processor such as a processor readable medium 160. In examples, the information processing device 120 may include micro-circuitry, processors, memory, and programmed algorithms to drive the transducer array 114 and process the signals acquired from the transducer array 114. In examples, a memory 162 for storing one or more algorithms may be included in information processing device 120 or may be a cloud storage which information processing device 120 may access. In examples, information processing device 120 may access cloud storage via wireless transmission device 150*a*. In examples, access to cloud storage may be gained via any other available and suitable means. In embodiments, the information processing device 120 may include one or more algorithms for beamforming and for interpreting the transducer signals.

In examples, the information processing device 120 and transducer 110 may be integral portions of the same device. In examples, the information processing device 120 may be physically separate from transducer 110. In examples, the information processing device 120 may be spatially separate and apart from transducer 110. In examples, information processing device may be in communication with transducer 110 via physical carrier or cable 140, via wireless transmission device 150, or a combination thereof.

As further illustrated in FIG. 1, diagnostic system 100 may include one or more displays 130 configured to output the imaging data. In examples, a display 130 may be an integrated display 130*a* of transducer 110. For example, integrated display 130*a* may be located at a surface of transducer 110 that is not contact surface 122. In examples, a display 130 may be an integrated display 130*b* of information processing device 120. In examples, one or more displays 130 may include a first display 130*a* as an integrated component of transducer 110 and a second display 130*b* as an integrated component of information processing device 120. In examples, a display 130 may be physically separate from transducer 110 and information processing device 120. In examples, a display 130 may be spatially separate and apart from transducer 110 and information processing device 120. In examples, a display 130 may be in communication with transducer 110, information processing device 120, or both. In examples, a display 130 may communicate with transducer 110 and/or information processing device 120 via a physical carrier or cable 142*a* and/or 142*b*, via wireless transmission device 150, or a combination thereof. In examples, a display 130 may include its own power supply 132*a* such as a battery or capacitor, be configured to connect to a power source 132*b*, be configured to be powered by transducer 110, be configured to be powered by information processing device 120, or any combination thereof.

In examples, a display 130 may include any suitable display device. For example, display 130 may include a liquid crystal display, a light emitting diode display, a plasma display, or any other suitable displays. In examples, a display 130 may function as input/output device. For example, a display 130 may include a touch screen display capable of receiving user inputs. In examples, information processing device 120 may be configured to receive and process any input command entered via a display 130.

Figure 2A:
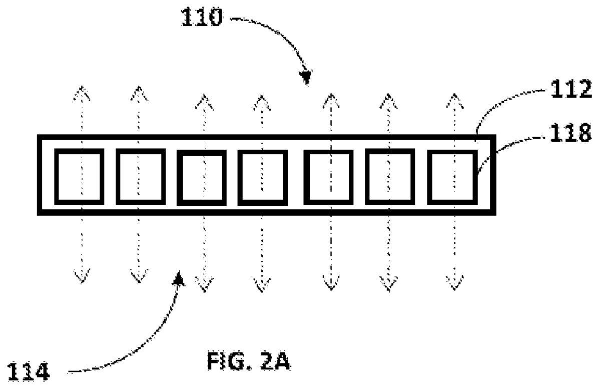
FIG. 2A schematically illustrates examples of transducer elements of a transducer array according to the present disclosure in an unflexed state.
Figure 2B:
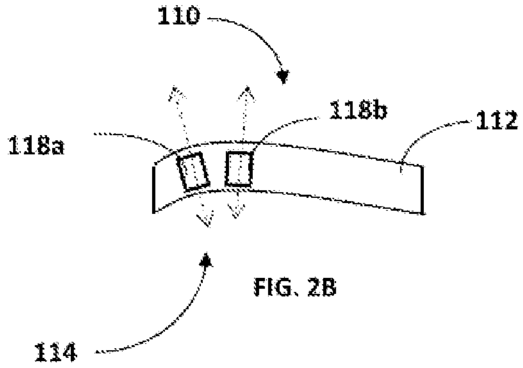
FIG. 2B schematically illustrates examples of transducer elements of a transducer array according to the present disclosure in a flexed state.

FIGS. 2A and 2B, are examples of schematic illustrations of a transducer 110 in a nominal state and an applied state, respectively. Referring to FIG. 2A, in the nominal state, such as an unused state before the transducer 110 is secured to a surface or patient, the transducer elements 118 of the transducer array 114 may have a known physical spacing and orientation relative to one another. That is, the distance or pitch between each of the transducer elements 118 of transducer array 114 may be known. In examples, the relative orientation of transducer elements 118 of transducer array 114 relative to each other and/or to housing 112 of transducer 110 may be known. For example, as illustrated in FIG. 2A, at a nominal state, transducer elements 118 of transducer array 114 may be arranged in parallel.

Referring to FIG. 2B, when applied to a surface, such as a portion of a body of a patient, the housing 112 may be deformed to confirm to the contour of the surface to which it is applied thereby affecting the position, i.e. the location, spacing and/or the orientation of the transducer elements 118. In examples, it should be appreciated that the change in position of the transducer elements 118 may be "arbitrary" because it may depend on the contour of the surface against which the transducer 110 is applied. The position of the transducer elements 118 when the transducer 110 is applied to a surface is considered arbitrary because the contour of the surface over which transducer 110 is to be applied may not be known beforehand or may vary depending on the surface, for example, different patients may have varying surface contours over which transducer 110 may be applied.

Figure 3:
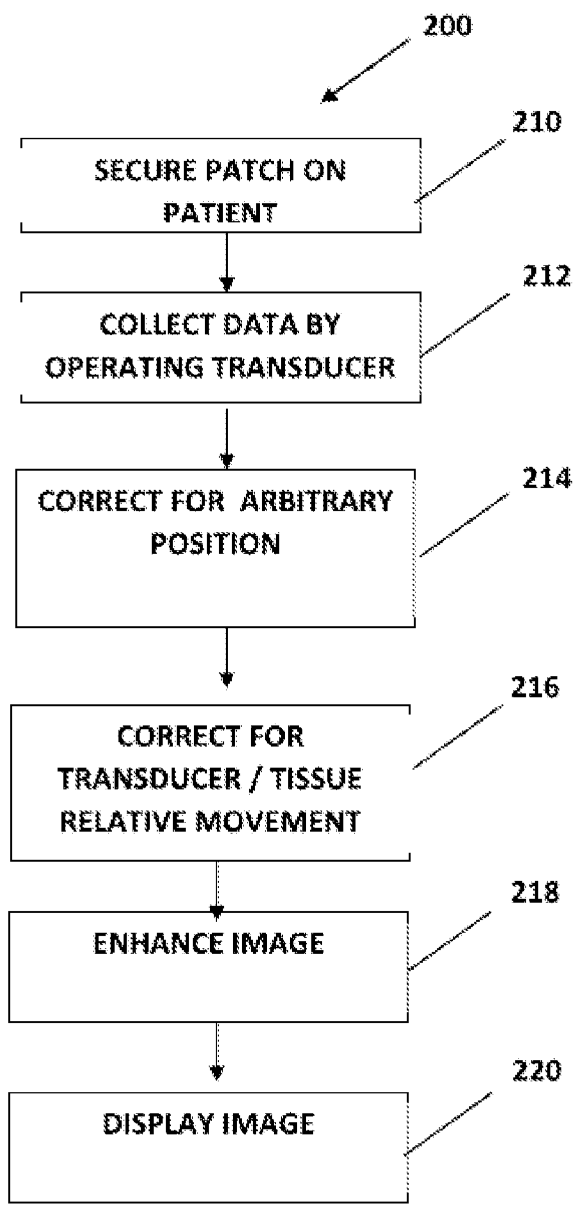
FIG. 3 illustrates a flow chart of an example method for performing a diagnostic analysis according to the present disclosure.

FIG. 3 illustrates an example of a method 200 for using the diagnostic system 100 illustrated in FIG. 1. In examples, the method of using diagnostic system 100 may provide a way to run a diagnostic on a patient or object. The method 200 may begin at 210 where a transducer 110 may be secured to a surface, for example to a selected region of the body of a patient. In examples, the selected region may be proximate to the expected location of an internal physical condition. In examples, the physical condition may be desirable or undesirable. For example, the physical condition may include an internal injury, a pregnancy, or any other condition.

In examples, at 210, the transducer 110 may be removably affixed to a surface. In examples, the transducer 110 may be secured in place by the one or more securing members 116. In examples, transducer 110 may be secured such that no additional physical manipulation or effort is needed to the keep the transducer 110 in place. In examples, once placed and secured, the transducer 110 may be stationary relative to a surface such as a cutaneous surface at a location on the body of a patient.

At 212, transducer 110 may be operated via the information processing device 120. In examples, transducer 110 may be operated to collect data. In examples, the data may be image data. In examples, the transducer 110 may be configured to emit ultrasonic signals and detect reflected ultrasonic signals. In examples, operation of transducer 110 may include causing transducer 110 to emit ultrasonic signals and detect reflected ultrasonic signals via the transducer array 114. In examples, when transducer 110 is affixed onto a patient, the ultrasonic signals may be emitted into an internal region of the body of the patient. In examples, when transducer 110 is affixed onto a patient, the detected ultrasonic signals are reflected at an internal region of the body of the patient.

In examples, during operation of transducer 110, there may be relative movement between the transducer array 114 and the internal organs or tissue of the patient due to breathing or other bodily functions. Further, because the housing 112 may have flexed or deformed to conform to the surface contour of the body of the patient, the spacing between individual transducer elements 118 of the transducer array 114 may have changed.

To address these issues, at 214 beamforming algorithms may be utilized to determine appropriate weights to compensate for the arbitrary positions (e.g., distance, spacing and/or orientation) of the individual transducer elements 118 when transducer 110 is affixed to a surface. In examples, sparse array and non-coherent beamforming techniques associated with synthetic aperture radar (SAR) may be used. In examples, one suitable technique may include using a priori information of the position of the transducer elements 118 at the transducer 110 nominal state, i.e. before application of the transducer 110 to the surface. In examples, machine learning may then be used to determine appropriate weights to compensate for movement and orientation when the transducer 110 is affixed to the surface.

In examples, another suitable technique may include using Iterative Maximum-a-Posteriori (iMAP). Using an iterative solver such as the conjugate gradient method to solve $$\mathrm{argmin}_x \|W(y - Ax)\|_2^2 - \log P(x).$$

Unequal spacing between transducer elements may be addressed using Super-SVA on sparse aperture. Algorithms may be configured to interpolate the collected data to fill gaps and to build a large aperture from a number of closely spaced sparse apertures. Filling the sparse aperture may provide better resolution. Thus, the correction may be done to reduce errors arising from changes in relative locations of the transducer elements 118, such as may occur if the spacing between transducers elements 118 increases when the transducer array 114 is stretched when transducer 110 is affixed to a surface. In examples, correction may be done to reduce errors arising from changes in relative orientation of the transducer elements 118, such as may occur during bending or twisting of the transducer array 114.

In examples, as shown at 216, beamforming algorithms may be utilized to address the change in distance between the individual transducer elements 118 and internal body tissue. For instance, a distance correction algorithm may be used to correct for changes in distance between the transducer elements and internal body tissue caused by a beating heart, lung movement, muscle spasms, voluntary movement, involuntary movement, etc. Merely as an analogy, the correction may be similar to correcting a focal distance of a camera. In examples, a motion correction algorithm may be used to correct for motion of an internal feature of interest relative to the transducer elements 118. The feature of interest may be bodily tissue and/or a fluid. Example features of interest include, but are not limited to, blood flow, urinary tract flow, diaphragm motion, etc. An internal feature of interest may be an externally introduced material or object.

In examples, at 218, one or more algorithms may be configured to provide visual enhancement of the information obtained from the transducer array 114. In examples, enhancement of the information can be achieved using a segmentation algorithm. Any standard segmentation algorithm may be used with the system described herein. In examples, segmentation can be accomplished by local variation techniques using modifications of Kruskal's algorithm. Kruskal's algorithm conventionally has been used for unsupervised segmentation of land features (water, terrain, and human-made objects) from SAR, electro-Optical, and Medical images. Segmentation techniques are also disclosed in J. Malik, S. Belongie, T. Leung, and J. Shi, *Contour and texture analysis for segmentation*, Int. J. of Computer Vision, 43(1):7-27, 2001 and P. F. Felzenszwalb and D. P. Huttenlocher, "*Image segmentation using local variation*," Proceedings. 1998 IEEE Computer Society Conference on Computer Vision and Pattern Recognition (Cat. No. 98CB36231), 1998, pp. 98-104, doi: 10.1109/CVPR.1998.698594, the contents of which are incorporated by reference for all purposes.

In examples, at 220, an enhanced image may be displayed to the user via a display 130 based on the image data collected by transducer 110 operated by information processing device 120. In examples, the image can be enhanced with sharpening, focusing, and/or apodization techniques. The image may be static or may be dynamic, i.e., a video. In examples, the imaging may be performed without requiring physical manipulating of transducer 110 and/or the transducer array 114 or transducer elements 118. Thus, in examples, a user who would otherwise be operating the transducer 110 to perform imaging, may be free to perform other activities why the diagnostic system 100 generates the imaging. In examples, diagnostic system 100 may not require specialized medical training. Thus, the diagnostic system 100 may be operated by users that do not have specialized medical training.

In examples, the entire diagnostic system 100 may be co-located. By co-located, it is meant with sufficient proximity to one another that a person may be able to physically access all of the components. In other embodiments, the components of the diagnostic system 100 may be distributed or provided at locations remote from each other. Thus, for example, the transducer 110 and the display device 130 may be located at a first location and the information processing device 120 may be located at a second different location. In examples, wireless transmission devices 150 (i.e. 150*a*, 150*b*, 150*c* . . . ) may be used to transmit information encoded signals between and among the various components. Thus, for example, signals from the transducer 110 may be transmitted from a remote area or vehicle to a central location where the information processing device 120 is positioned. Processed information from the information processing device 120 may be sent to a display 130, which may be at the remote area or vehicle or at a separate location. In examples, the information processing device 120 may include two or more information processing devices 120. For example, a central information processing device 120 may communicate with and/or control two or more transducers 110. In examples, both the remote location or vehicle and the central location may have an information processing device 120, a display 130 or any combination thereof that can work with one or more transducers 110.

Figure 4:
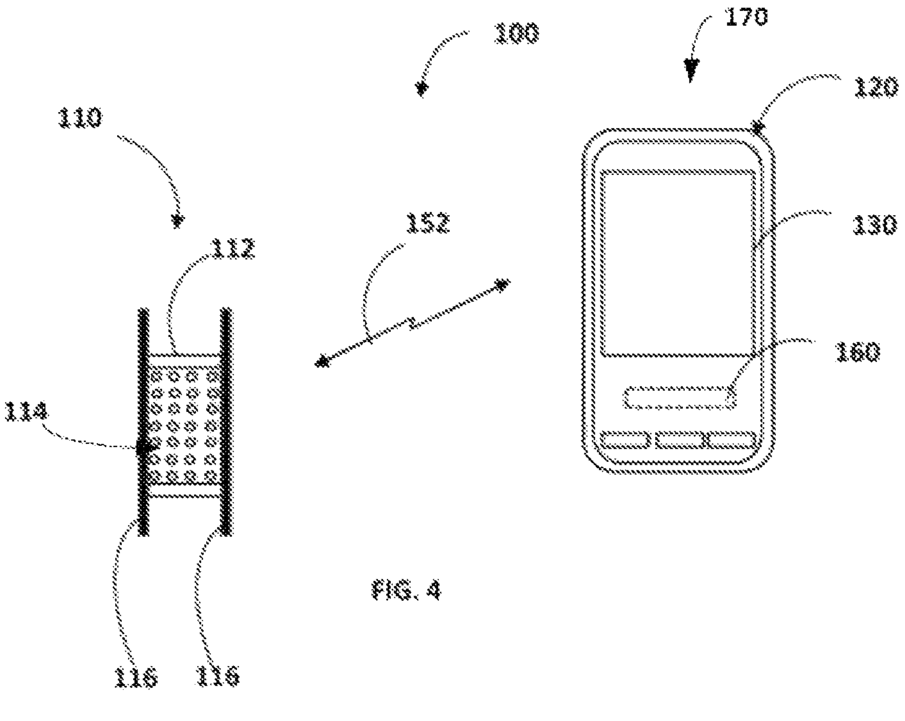
FIG. 4 schematically illustrates another embodiment of a diagnostic system according to the present disclosure.

FIG. 4 illustrates another example of a diagnostic system 100. As shown, diagnostic system 100 may include a wearable transducer 110, an information processing device 120, and a display 130. Information encoded signals 152 may be exchanged between information processing device 120 and the transducer 110 using wireless telemetry such as wi-fi, Bluetooth, or radio as previously described. Electrical power may be provided by suitable power sources such as batteries or by connection to a power source. The transducer 110 may include a housing 112, a transducer array 114 of transducer elements 118, and one or more securing members 116. In examples, the information processing device 120 may include a processor-readable medium 160 having a machine-readable program embedded therein and accessible to one or more processors in the information processing device 120. In examples, the information processing device 120 may be a cellular telephone, a laptop, or a "tablet" type of device. Instructions on information processing device 120 may be in the form of software and/or hardware. In an example, information processing device 120 may be a smart device 170, such as a smart phone. In examples, the instructions to allow the mobile phone to communicate and/or control transducer 110 and to optionally process collected image data may be in the form of an application installed on the smart phone. In examples, an application on a smart device may allow the smart device to work as an intermediary between a remote information processing device 120 and a transducer 110. In examples, at least some but not all functions of the information processing device 120 may be performed on the smart device leaving the remaining functions to a remote information processing device 120. In examples, as illustrated, a display 130 may also be part of the same device as information processing device 120. For example, the information processing device 120 and a display 130 may be components of the same smart device, such as a smart phone.

In examples, although not shown, the one or more control systems may include one or more controllers and/or other suitable computing devices may be employed to control one or more of portions of systems described herein. Controllers may include one or more processors and memory communicatively coupled with each other. In the illustrated example, a memory may be used to store logic instructions to operate and/or control and/or monitor the operation of the diagnostic system 100 or a subcomponent thereof. In examples, the controllers may include or be coupled to input/output devices such as monitors, keyboards, speakers, microphones, computer mouse and the like. In examples, the one or more controllers may also include one or more communication components such as transceivers or like structure as described to enable wired and/or wireless communication. In examples, this may allow for remote operation of one or more systems described herein.

In examples, memory associated with the one or more controllers and/or other suitable computing devices may be non-transitory computer-readable media. The memory may store an operating system and one or more software applications, instructions, programs, and/or data to implement the methods described herein and the functions attributed to the various systems. In various implementations, the memory may be implemented using any suitable memory technology, such as static random-access memory (SRAM), synchronous dynamic RAM (SDRAM), nonvolatile/Flash-type memory, or any other type of memory capable of storing information. The controls systems may include any number of logical, programmatic, and physical components.

Logic instructions may include one or more software modules and/or other sufficient information for autonomous operation, safety procedures, and routine maintenance processes. Any operation of the described system may be implemented in hardware, software, or a combination thereof. In the context of software, operations represent computer-executable instructions stored on one or more computer-readable storage media that, when executed by one or more processors, perform the recited operations. Generally, computer-executable instructions include routines, programs, objects, components, data structures, and the like that perform one or more functions or implement particular abstract data types.

From the above, it should be appreciated that the teachings of the present disclosure, including non-coherent beamforming techniques, may be readily applied to the medical ultrasound array. Utilizing the present teachings may result in a decrease in the data volume requirements for image reconstruction, reduce data rate requirements for transmission, and the potential to increase sensitivity.

While the foregoing is directed to embodiments of the present disclosure, other and further embodiments of the disclosure may be devised without departing from the basic scope thereof, and the scope thereof is determined by the claims that follow.

What is claimed is:

1. An ultrasonic diagnostic system, comprising:
a single transducer comprising:
a deformable housing configured to conform to a surface contour of a selected region;
one or more securing members configured to removably affix the deformable housing to a surface; and
an ultrasonic transducer array disposed in the deformable housing and comprising a plurality of transducer elements configured to assume arbitrary positions when the housing is deformed,
wherein the transducer elements are arranged at a pitch of about 450 μm to 710 μm, and a center frequency for the transducer array is from about 1.2 MHz to about 5.7 MHz, and
wherein the transducer is configured to collect image data while in a fixed position and to communicate the image data to an information processing device that comprises at least a beamforming algorithm or an image enhancement algorithm.

2. The ultrasonic diagnostic system of claim 1, wherein each transducer element of the ultrasonic transducer array is movable relative to one another.

3. The ultrasonic diagnostic system of claim 1, wherein the beamforming algorithm is configured to correct for: (i) changes in relative locations of one or more of the plurality of transducer elements of the transducer array, and (ii) changes in relative orientations of one or more of the plurality of the transducer elements.

4. The ultrasonic diagnostic system of claim 1, wherein the information processing device further comprises a distance correction algorithm configured to correct for changes in distance between one or more of the plurality of transducer elements and internal body tissue.

5. The ultrasonic diagnostic system of claim 1, wherein the information processing device further comprises a motion correction algorithm configured to correct for a displacement of an internal feature below the surface contour and one or more of the plurality of transducer elements.

6. The ultrasonic diagnostic system of claim 1, wherein the information processing device further comprises a motion correction algorithm configured to correct for a displacement of a feature of interest inside a body of a patient, wherein the feature of interest comprises: (i) bodily tissue, or (ii) a fluid.

7. The ultrasonic diagnostic system of claim 1, wherein the image enhancement algorithm is configured to perform segmentation of an image.

8. The ultrasonic diagnostic system of claim 1, further comprising a display device in signal communication with the information processing device.

9. A method for collecting image data, comprising:
securing a single transducer to a selected location, the transducer comprising a deformable housing, at least one securing member, and an ultrasonic transducer array comprising a plurality of transducer elements having a center frequency ranging from about 1.2 MHz to about 5.7 MHz and disposed within the deformable housing arranged at a pitch of about 450 μm to 710 μm;
collecting image data by operating the transducer via an information processing device while keeping the transducer stationary relative to the selected location;
correcting the collected image data using at least one beamforming algorithm, wherein the at least one beamforming algorithm corrects for arbitrary positions of one or more of the plurality of transducer elements of the ultrasonic transducer array; and
enhancing an image representative of the collected image data using at least one image enhancement algorithm to provide an enhanced image.

10. The method of claim 9, further comprising displaying the enhanced image on a display device.

11. The method of claim 9, wherein the securing the transducer comprises one of: (i) securing the transducer using an adhesive, and (ii) compressing the transducer to the selected location using a band.

12. The method of claim 9, further comprising correcting the image data collected to reduce errors arising from relative motion between the transducer and a region of interest below a surface of the selected location.

13. The method of claim 9, wherein the selected location comprises a body region of a patient and the transducer is secured to a cutaneous surface of the body of the patient.

14. The method of claim 13, further comprising correcting the image data collected to reduce errors arising from relative motion between the transducer and an internal organ within the body of the patient.

15. A non-transitory computer-readable medium having a machine program embedded therein and accessible to at least one processor for executing the machine program, the at least one processor being associated with a single transducer configured to acquire image data below a selected surface, wherein the single transducer comprises an ultrasonic transducer array having a plurality of transducer elements arranged at a pitch of about 450 μm to 710 μm, wherein the machine program comprises:
instructions to operate the transducer at a center frequency ranging from about 1.2 MHz to about 5.7 MHz and to collect image data;
instructions to correct the collected image data for arbitrary positions of the transducer elements of the ultrasonic transducer array; and
instructions to enhance an image representative of the collected image data.

16. The non-transitory computer-readable medium of claim 15, wherein the transducer is configured to acquire image data representative of internal body tissue.

* * * * *